United States Patent [19]

Herscovici

[11] Patent Number: 4,586,507
[45] Date of Patent: May 6, 1986

[54] DUAL CHANNEL CARDIAC PACER ISOLATION CIRCUIT

[75] Inventor: Harry Herscovici, Miami Beach, Fla.

[73] Assignee: Cordis Corporation, Miami, Fla.

[21] Appl. No.: 657,971

[22] Filed: Oct. 4, 1984

[51] Int. Cl.⁴ ............................................. A61N 1/36
[52] U.S. Cl. ............................................. 128/419 PG
[58] Field of Search ................................. 128/419 PG

[56] References Cited

U.S. PATENT DOCUMENTS

| | | | |
|---|---|---|---|
| 3,669,120 | 6/1972 | Nielsen | 128/419 PG |
| 3,815,109 | 6/1974 | Carraway et al. | 128/903 |
| 3,903,897 | 9/1975 | Woollons et al. | 128/419 PG |
| 4,114,627 | 9/1978 | Lewyn et al. | 128/419 PG |
| 4,300,566 | 11/1981 | Stindt et al. | 128/419 PG |
| 4,402,322 | 9/1983 | Duggan | 128/419 PG |
| 4,462,406 | 7/1984 | DeCote, Jr. | 128/419 PG |
| 4,462,407 | 7/1984 | Herscovici et al. | 128/419 PG |
| 4,470,418 | 9/1984 | Herscovici et al. | 128/419 PG |

Primary Examiner—William E. Kamm
Assistant Examiner—Mitchell J. Shein
Attorney, Agent, or Firm—George H. Gerstman

[57] ABSTRACT

A system is provided for preventing cross-stimulation between the atrium and ventricle during cardiac pacing using a dual chamber cardiac pacer. A first output capacitor is connected in series with the atrium lead and a second output capacitor is connected in series with the ventricle lead. The first output capacitor is isolated from being charged until an atrial stimulus pulse is issued and the second output capacitor is isolated from being charged until a ventricle stimulus pulse is issued. The isolation means comprises analog switches that are controlled by a pacer logic circuit so that a current flow line is provided to the first output capacitor only when a stimulus pulse is issued to the atrium and a current flow line is provided to the second output capacitor only when a stimulus pulse is issued to the ventricle.

9 Claims, 2 Drawing Figures

DUAL CHANNEL CARDIAC PACER ISOLATION CIRCUIT

BACKGROUND OF THE INVENTION

The invention relates generally to cardiac pacers, and more particularly to means for preventing crosstalk between bipolar pacer leads.

There are two major pumping chambers in the heart, the left and right ventricles. Simultaneously contracting, these chambers expel blood into the aorta and the pulmonary artery. Blood enters the ventricles from the left and right atria, respectively. The contractions arise from a wave of electrical excitation which begins in the right atrium and spreads to the left atrium. The excitation enters the atrio-ventricular (AV) node which delays its passage via the bundle of His into the ventricles. The atria contract in a separate action which precedes the major ventricular contraction by an interval of about 100 milliseconds (md), known as the AV delay. In the healthy heart, atrial contractions begin every 400–1,000 ms at a steady metabolically determined frequency known as the "sinus" rate, which increases automatically with exercise, the AV delay being foreshortened at higher rates.

Electrical signals corresponding to the contractions appear in the electrocardiogram. A signal known as the P-wave accompanies the atrial contraction while a signal known as the QRS complex, with a predominant R-wave, accompanies the ventricular contraction. The P and R-waves can be reliably detected as timing signals by electrical leads in contact with the respective heart chambers.

The typical implanted cardiac pacer operates by producing electrical stimulation pulses to supply missing excitation via an insulated wire (or "pacing lead") terminating in an electrode attached to the right ventricle. The R-wave can be sensed by the same lead to inhibit or trigger stimulation or to restart a timing interval as in "demand" pacing. An additional lead contacts the atrium to sense P-waves, if desired. Pacers whose ventricular stimulation is timed from the sensing of a P-wave are referred to as synchronous or "physiological" pacers since they preserve the natural sinus rate as well as the normal sequence of contractins. In AV sequential pacers, sometimes the atrial lead is also used for atrial stimulation.

There are two basic types of electrode systems used in pacing leads. Unipolar leads terminate distally in a single electrode (cathode) and employ the case of the pulse generator itself, or a conductive plate on the case, as the return electrode or ground (anode). Bipolar pacing leads, on the other hand, terminate distally in two spaced insulated electrodes connected to the pulse generator through respective wires in the pacing lead. Thus, each bipolar lead carries a positive and negative electrode for the respective chamber, and the case is not designed to form a part of the electrical circuit in this configuration.

In an AV sequential bipolar lead pacing system, bipolar pacing leads extend into the right atrium and right ventricle. In a pacer having a common ground connection, the two positive electrodes on the respective bipolar leads are tied together electrically. This shared ground connection can present crosstalk problems in both sensing and stimulation when each bipolar lead is in a different heart chamber. This is an extremely important problem to solve for physiological pacers which provide bipolar stimulation and sensing for both heart chambers with the same implanted pacer powered by a single battery.

One of the ways previously used to accomplish some measure of isolation between bipolar leads is to employ a transformer in the output stage of the pacing circuit to isolate the lead electrodes. This approach, however, has only been practical when sensing is done only one one channel. In addition, it has the serious drawback of adding a relatively bulky ineffecient component to the otherwise miniaturized pacer electronics.

In U.S. application Ser. No. 375,040, filed May 5, 1982, and assigned to the assignee of the present invention, in order to prevent crosstalk between atrial and ventricular bipolar cardiac pacer leads, separate input/output circuits for the two channels are powered by respective isolated capacitors. In one embodiment, the capacitors are resistively coupled to the pacer battery for continuous charging. In another embodiment, one side of each capacitor is normally disconnected from the pacer battery. Charging switches momentarily connect one or the other capacitor directly to the battery in response to the output of the corresponding sense amplifier.

In U.S. application Ser. No. 375,198, filed May 5, 1982, and assigned to the assignee of the present invention, interchannel crosstalk in an existing dual channel pacer designed for bipolar leads is reduced by inserting a switching circuit between the pacing leads and the pacing terminals. In one embodiment, in each channel an isolation resistance and buffer amplifier in series with the lead electrodes, respectively, are shunting during stimulation. In another embodiment, the lead electrodes are connected to a pair of differential amplifiers which are bipassed during stimulation on a given channel.

I have discovered a system that improves upon and simplifies the aforementioned isolation circuits, may be used with most existing pacers, and is useful to obviate any cross-stimulation between the two pacer channels in any correct or incorrect lead connection.

SUMMARY OF THE INVENTION

In accordance with the present invention, a system is provided for preventing cross-stimulation between the atrium and ventricle during cardiac pacing using a dual chamber cardiac pacer having a battery power supply, a pacing lead connected to the atrium and a pacing lead connected to the ventricle. The system includes a first output capacitor connected in series with the atrium lead and a second output capacitor connected in series with the ventricle lead. A pulse generator is operatively connected to the first output capacitor for providing a stimulus pulse through the first output capacitor to the atrium and is operatively connected to the second output capacitor for providing a stimulus pulse through the second output capacitor to the ventricle. The first capacitor is isolated from being charged and the atrium lead is isolated until an atrial stimulus pulse is issued. Likewise, the second output capacitor is isolated from being charged and the ventricle lead is isolated until a ventricle stimulus pulse is issued.

In the illustrative embodiment, the isolation circuit comprises a first switch connected between the battery power supply and the first output capacitor to prevent the first output capacitor from being charged until the first switch is operated to provide a current flow line to the first output capacitor. In addition, a second switch is connected between the battery power supply and the second output capacitor to prevent the second output capacitor from being charged until the second switch is operated to provide a current flow line to the second output capacitor. A pacer logic circuit controls the operation of the pulse generator and the first and second switches so that the first switch is operable to provide a current flow line to the first output capacitor only when a stimulus pulse is issued to the atrium and the second switch is operable to provide a current flow line to the second output capacitor only when a stimulus pulse is issued to the ventricle.

A more detailed explanation of the invention is provided in the following description and claims, and is illustrated in the accompanying drawings.

DETAILED DESCRIPTION OF THE ILLUSTRATIVE EMBODIMENT

Figure 1:
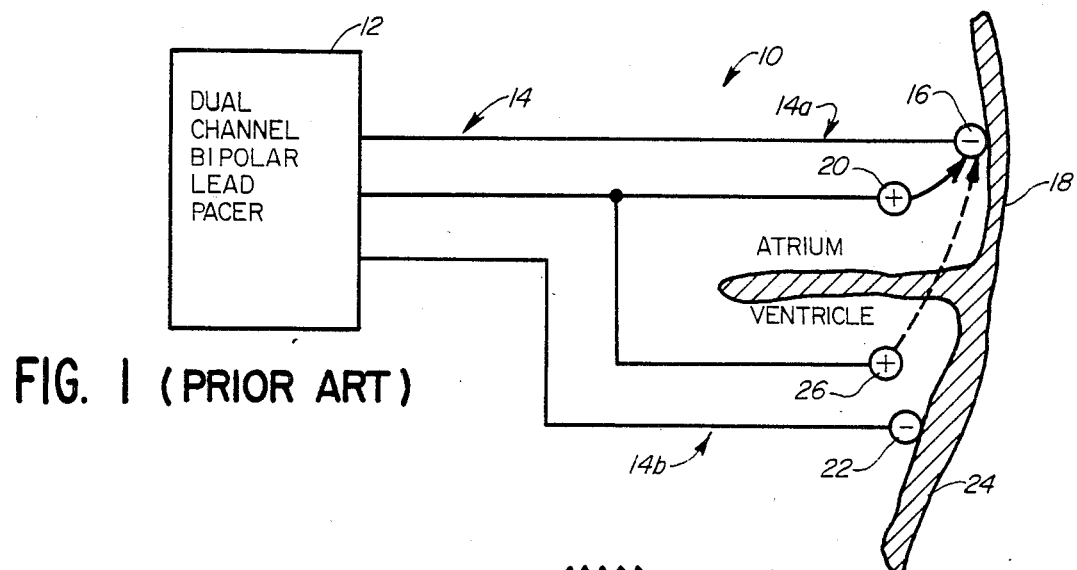
FIG. 1 is a schematic representation of a prior art dual channel bipolar lead pacer system.

FIG. 1 shows an AV sequential bipolar lead pacing system 10 including a double demand cardiac pacer pulse generator 12 containing the pacing logic circuitry sealed together with the battery cells in the customary biologically compatible hermetic enclosure. The pacer pulse generator 12 itself is implanted at a suitable location in the body, such as the auxillary region, and is electrically interconnected with a three conductor pervenous pacer lead 14 which terminates in an atrial lead 14a having a negative electrode 16 in contact with the inside of the right atrium 18 and a positive electrode or anode 20 spaced from the cathode. The ventricular portion 14b of the pacer lead terminates in a negative electrode 22 in contact with the ventricular wall 24 and a spaced anode 26. The anodes 20 and 26 share a common electrical connection and are thus at the same reference potention. In sensing, a "spurious" electrical potential can be established by the heart itself between the ventricular anode 26 and the atrial cathode 16 resulting in a signal to the pacer which appears to have originated in the atrium alone. The electrical path between atrial electrode 16 and 20 offers less resistance, of course, and is therefore the expected site of stimulation when the pacer pulse generator 12 applies an electrical potential between these electrodes. However, the ventricular anode 26 may inadvertently become part of the electrical circuit and cause undesirable cross-stimulation. The same type of crosstalk on sensing or stimulation can occur on the ventricular channel through cathode 22 in relation to anodes 20 and 26.

Figure 2:
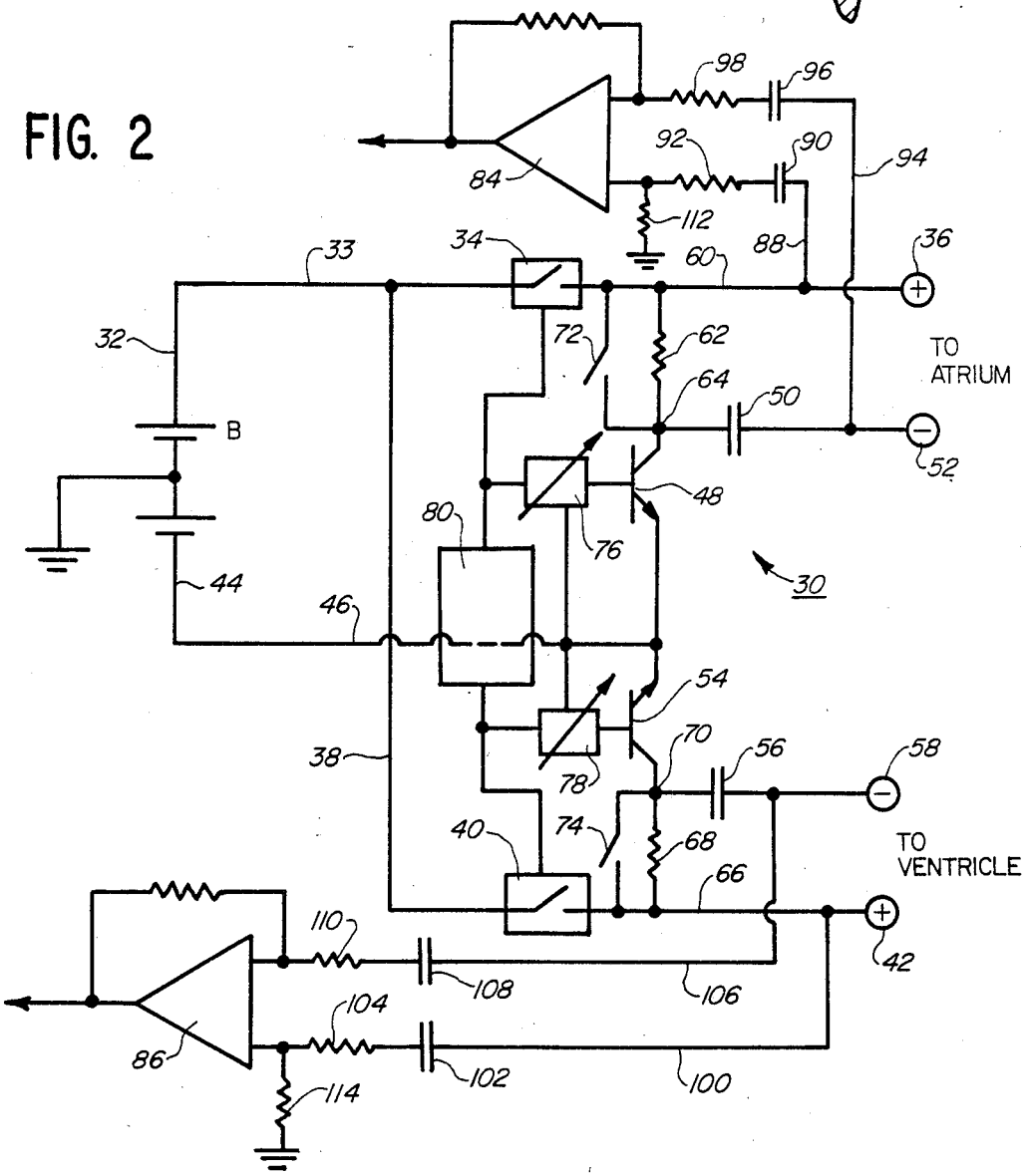
FIG. 2 is a schematic and block diagram of a dual channel cardiac pacer isolation circuit constructed in accordance with the principles of the present invention.

The circuit of FIG. 2 provides a solution to this problem in the context of an existing three terminal implantable pacer 30. The battery B which powers the pacer has its positive terminal 32 (reference potential) connected via line 33 through an analog switch 34 to a positive output terminal 36 and also connected via line 38 and through a second analog switch 40 to positive output terminal 42. Negative terminal 44 of battery B is connected via line 46, transistor 48 and a first output capacitor 50 to negative output terminal 52. Terminal 44 is also connected via line 46, transistor 54 and second output capacitor 56 to negative output terminal 58. A bipolar lead (not shown) is connected from terminals 36 and 52 to the atrium and another bipolar lead (not shown) is connected from terminals 42 and 58 to the ventricle.

Analog switch 34 is connected to output terminal 36 via line 60 and a resistor 62 is connected between line 60 and the junction 64 of the collector of NPN transistor 48 and first output capacitor 50. Likewise, second analog switch 40 is connected to output terminal 42 via line 66 and a resistor 68 is connected between line 66 and the junction 70 of the collector of NPN transistor 54 and second output capacitor 56. A first charge dump switch 72 is connected in parallel with resistor 62 and a second charge dump switch 74 is connected in parallel with resistor 68.

An atrial amplitude adjustment circuit 76 is connected to the base of transistor 48 and an atrial amplitude adjustment circuit 78 is connected to the base of transistor 54.

Analog switches 34 and 40, and transistors 48 and 54, are controlled by a pacer logic circuit 80. Analog switch 34 is normally open and is operated by pacer logic circuit 80 to close only when an atrial stimulus pulse is issued. Likewise, analog switch 40 which is controlled by pacer logic circuit 80 is normally open and is operated by pacer logic circuit 80 to close only when a ventricle stimulus pulse is issued. Thus unless a control signal is provided by the pacer logic circuit 80, switches 34 and 40 will remain open. Switches 34 and 40 will close only when there is a control signal provided by logic circuit 80 to the switches and at the same time to the amplitude adjustment circuits 76 and 78 and respective output transistors 48 and 54. Thus switch 34 will close only at the same time that transistor 48 becomes conductive and a pulse will be provided to the atrium in the conventional manner. Likewise, switch 40 will be operated to close only at the same time that transistor 54 is conductive and a pulse will be provided to the ventricle in the conventional manner. In effect, switch 34 is responsive to the atrium stimulus pulse and switch 40 is responsive only to the ventricle stimulus pulse. By locating switch 34 in the supply line of the atrial output stage transistor 48 and by locating switch 40 in the supply line of the ventricle output stage transistor 54, cross-stimulation is prevented. By having switch 34 on the input side of transistor 48, capacitor 50 does not charge until an atrial stimulus pulse is issued. Likewise, by having switch 40 on the input side of transistor 54, capacitor 56 does not charge until a ventricle stimulus pulse is issued. Charge dump switches 72 and 74 are also operated by pacer logic circuit 80.

The illustrated system operates to isolate capacitor 50 from being charged during ventricle stimulation and completely isolates capacitor 56 from being charged during atrial stimulation. Thus crosstalk is prevented from occurring because there is no connection between the respective leads or the output capacitors of both chambers.

The only coupling that is not completely isolated is the input circuits to atrium sense amplifier 84 and ventricle sense amplifier 86. Sense amplifier 84 is connected to positive terminal 36 via line 88 having capacitor 90 and resistor 92 in series therewith. Amplifier 84 is connected to negative terminal 52 via line 94 having capacitor 96 and resistor 98 in series therewith. Ventricle sense amplifier 86 is connected to positive terminal 42 via line 100 having capacitor 102 and resistor 104 in series therewith. The ventricle sense amplifier 86 is connected to negative terminal 58 via line 106 having capacitor 108 and resistor 110 in series therewith. Sense amplifiers 84 and 86 are differential amplifiers and it can be seen that the input circuit of amplifier 84 is connected to ground via resistor 114. In order to isolate the "leak" between terminal 36 and terminal 42 through the input resistors of the sense amplifiers 84 and 86, resistors 92, 112, 104 and 114 are a high resistance and, ideally, the resistance of resistor 92 is equal to the resistance of resistor 104 while the resistance of resistor 112 is equal to the resistance of resistor 114. It is further preferable to limit the A-V cross-current to 0.05 milliamps.

It is seen that an isolation circuit has been provided by utilizing switches in series with the output lines that are closed only during the duration of the stimulus pulse that is issued to the respective chamber. Thus switch 34 is closed only during the time that a stimulus pulse is issued to the atrium and remains open during all other times. Likewise, switch 40 is closed only during the period of time that a stimulus is issued to the ventricle, and it remains open at all other times.

Although an illustrative embodiment of the invention has been shown and described, it is to be understood that various modifications and substitutions may be made by those skilled in the art without departing from the novel spirit and scope of the present invention.

What is claimed is:

1. A system for preventing cross-stimulation between the atrium and ventricle during cardiac pacing using a dual chamber cardiac pacer having a battery power supply, a pacing lead connected to the atrium and a pacing lead connected to the ventricle, which comprises:
   a first output capacitor connected in series with said atrium lead;
   a second output capacitor connected in series with said ventricle lead;
   pulse generating means operatively connected to said first output capacitor for providing a stimulus pulse through said first output capacitor to the atrium and operatively connected to said second output capacitor for providing a stimulus pulse through said second output capacitor to the ventricle;
   a first switch connected between the battery power supply and said first output capacitor to prevent said first output capacitor from being charged until said first switch is operated to provide a current flow line to said first output capacitor;
   a second switch connected between the battery power supply and said second output capacitor to prevent said second output capacitor from being charged until said second switch is operated to provide a current flow line to said second output capacitor; and
   pacer logic means for controlling the operation of said pulse generating means and said first and second switches so that said first switch is operable to provide a current flow line to the first output capacitor only when a stimulus pulse is issued to the atrium and said second switch is operable to provide a current flow line to the second output capacitor only when a stimulus pulse is issued to the ventricle.

2. A system as described in claim 1, said pulse generating means including a first transistor operatively connected to said pacer logic means through an atrial amplitude adjustment circuit for providing an atrial stimulus pulse; and a second transistor operatively connected to said pacer logic means through a ventricle amplifier adjustment circuit for providing a ventricular stimulus pulse.

3. A system as described in claim 1, said first and second switch means each comprising an analog switch connected to said pacer logic means.

4. A system as described in claim 1, including a first charge dump switch connected to said first output capacitor and a second charge dump switch connected to said second output capacitor.

5. A system for preventing cross-stimulation between the atrium and ventricle during cardiac pacing using a dual chamber cardiac pacer having a battery power supply, a pacing lead connected to the atrium and a pacing lead connected to the ventricle, which comprises:
   a first output capacitor connected in series with said atrium lead;
   a second output capacitor connected in series with said ventricle lead;
   pulse generating means operatively connected to said first output capacitor for providing a stimulus pulse through said first output capacitor to the atrium and operatively connected to said second output capacitor for providing a stimulus pulse through said second output capacitor to the ventricle;
   a first switch connected between the battery power supply and said first output capacitor to prevent said first output capacitor from being charged until said first switch is operated to provide a current flow line to said first output capacitor;
   a second switch connected between the battery power supply and said second output capacitor to prevent said second output capacitor from being charged until said second switch is operated to provide a current flow line to said second output capacitor;
   pacer logic means for controlling the operation of said pulse generating means and said first and second switches so that said first switch is operable to provide a current flow line to the first output capacitor only when a stimulus pulse is issued to the atrium and said second switch is operable to provide a current flow line to the second output capacitor only when a stimulus pulse is issued to the ventricle;
   said pulse generating means including a first transistor operatively connected to said pacer logic means through an atrial amplitude adjustment circuit for providing an atrial stimulus pulse, and a second transistor operatively connected to said pacer logic means through a ventricle amplitude adjustment circuit for providing a ventricular stimulus pulse;
   a first charge dump switch connected to said first output capacitor and a second charge dump switch connected to said second output capacitor;
   said first switch comprising a normally open switch that is closed by said pacer logic means only during the issuance of the atrial stimulus pulse and said second switch is a normally open switch that is closed by said pacer logic means only during the issuance of the ventricular stimulus pulse.

6. A system as described in claim 5, said first and second switch means each comprising an analog switch connected to said pacer logic means and controlled thereby.

7. A system for preventing cross-stimulation between the atrium and ventricle during cardiac pacing using a dual chamber cardiac pacer having a battery power supply, a pacing lead connected to the atrium and a pacing lead connected to the ventricle, which comprises:

a first output capacitor connected in series with said atrium lead;

a second output capacitor connected in series with said ventricle lead;

pulse generating means operatively connected to said first output capacitor for providing a stimulus pulse through said first output capacitor to the atrium and operatively connected to said second output capacitor for providing a stimulus pulse through said second output capacitor to the ventricle;

means for isolating said first output capacitor from being charged and for isolating said atrium lead until an atrial stimulus pulse is issued; and means for isolating said second output capacitor from being charged and for isolating said ventricle lead until a ventricle stimulus pulse is issued.

8. A system as described in claim 7, said isolation means comprising a first switch connected between the battery power supply and said first output capacitor to prevent said first output capacitor from being charged until said first switch is operated to provide a current flow line to said first output capacitor, and a second switch connected between the battery power supply and said second output capacitor to provide said second output capacitor from being charged until said second switch is operated to provide a current flow line to said second output capacitor.

9. A system as described in claim 7, including pacer logic means for controlling the operation of said pulse generating means and said first and second switches so that said first switch is operable to provide a current flow line to the first output capacitor only when a stimulus pulse is issued to the atrium and said second switch is operable to provide a current flow line to the second output capacitor only when a stimulus pulse is issued to the ventricle.

* * * * *